United States Patent [19]

New et al.

[11] Patent Number: 4,524,206

[45] Date of Patent: Jun. 18, 1985

[54] 1-HETEROARYL-4-(2,5-PYRROLIDINE-DION-1-YL)ALKYL)PIPERAZINE DERIVATIVES

[75] Inventors: James S. New; Joseph P. Yevich, both of Evansville, Ind.

[73] Assignee: Mead Johnson & Company, Evansville, Ind.

[21] Appl. No.: 531,519

[22] Filed: Sep. 12, 1983

[51] Int. Cl.³ .................. C07D 403/14; C07D 31/495
[52] U.S. Cl. .................................. 544/230; 544/295; 544/364; 544/368; 544/372; 548/411; 548/545; 549/331; 549/477; 260/465 D; 260/465 H; 562/489
[58] Field of Search ................ 544/230, 295, 368, 364

[56] References Cited

U.S. PATENT DOCUMENTS

| | | | |
|---|---|---|---|
| 3,398,151 | 8/1968 | Wu | 424/250 |
| 3,558,777 | 1/1971 | Wu | 424/250 |
| 3,717,634 | 2/1973 | Wu et al. | 544/230 |
| 3,907,801 | 9/1975 | Wu et al. | 544/230 |
| 3,976,776 | 8/1976 | Wu et al. | 424/251 |
| 4,305,944 | 12/1981 | Temple, Jr. et al. | 544/230 |
| 4,361,565 | 11/1982 | Temple, Jr. et al. | 544/365 |
| 4,411,901 | 10/1983 | Temple, Jr. et al. | 544/230 |
| 4,452,799 | 6/1984 | Temple, Jr. et al. | 544/230 |

OTHER PUBLICATIONS

Wu, et al., "J. Med. Chem.", vol. 12, 1969, pp. 876–888.
Wu, et al., "J. Med. Chem.", vol. 15, 1972, pp. 477–479.

*Primary Examiner*—Glennon H. Hollrah
*Assistant Examiner*—James H. Turnipseed
*Attorney, Agent, or Firm*—Richard P. Ryan; Robert H. Uloth

[57] ABSTRACT

Disubstituted N,N'-piperazinyl derivatives are disclosed wherein one substituent is heteroaryl and the other is alkylene attached to the ring nitrogen of substituted 2,5-pyrrolidinedion-1-yl moieties. The substitution pattern of the pyrrolidinedione ring involves either geminal disubstitution, including spiro ring fusion, or 3,4-phenyl ring fusion to give phthalimide derivatives. Heteroaryl substitution on the other piperazine nitrogen comprises pyridine, pyrimidine, and benzisothiazole ring systems. Representative examples of these compounds demonstrate useful central nervous system effects.

23 Claims, No Drawings

1-HETEROARYL-4-(2,5-PYRROLIDINEDION-1-YL)ALKYL)PIPERAZINE DERIVATIVES

BACKGROUND OF THE INVENTION

This invention generally pertains to heterocyclic carbon compounds having drug and bio-affecting properties and to their preparation and use. In particular, the invention is concerned with 1,4-disubstituted piperazine derivatives wherein one substituent is a substituted 2,5-pyrrolidinedione ring system attached through its nitrogen atom via an alkylene chain and the other substituent is a heterocycle comprising pyridine, pyrimidine, or benzisothiazole.

Related art can be generalized by compounds of the following structural type:

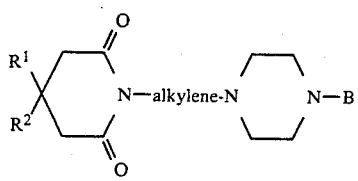

which are essentially glutarimide derivatives wherein $R^1$ and $R^2$ are alkyl or are joined to form $C_4$ or $C_5$ alkylene bridges and B represents aromatic or heteroaromatic systems with optional substituents. These and related compounds have been prepared as psychotropic agents and are described in the following references.

Compounds of the above depicted structure wherein B is a substituted or unsubstituted phenyl, pyridyl, or pyrimidinyl moiety are described in:

Wu, U.S. Pat. No. 3,398,151 patented Aug. 20, 1968.
Wu, U.S. Pat. No. 3,558,777 patented Jan. 26, 1971.
Wu, et al., J. Med. Chem., 12, 876–888 (1969); 15, 447–479 (1972).
Wu, et al., U.S. Pat. No. 3,717,634 patented Feb. 20, 1973.
Wu, et al., U.S. Pat. No. 3,796,776 patented Aug. 24, 1976.
Temple, et al., U.S. Pat. No. 4,361,565 patented Nov. 30, 1982.
Temple, co-pending application Ser. No. 334,688, filed Dec. 28, 1981.

Attention is also called to the co-pending application of Temple, Ser. No. 333,830, filed Dec. 23, 1981 wherein B is disclosed as being benzisothiazole. Also disclosed in this application are some compounds wherein the other piperazine substituent can be 2,4-thiazolidinediones or spiro substituted 2,4-thiazolidinediones connected at their nitrogen atom via an alkylene chain to the piperazine ring.

None of the aforementioned references disclose or suggest the compounds of the instant invention whose structures comprise substituted 2,5-pyrrolidinediones.

SUMMARY OF THE INVENTION

This invention is concerned with a new series of CNS-active compounds characterized by the following general structural formula (I)

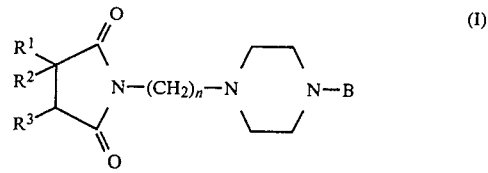

and the pharmaceutically acceptable acid addition salts thereof. In the foregoing formula, $R^1$ is $C_{1-4}$ alkyl, trifluoromethyl, Z-substituted phenyl with Z being hydrogen or halogen, or $R^1$ can be taken together with $R^2$ as a $C_{4-5}$ alkylene bridge incorporating a fused Z-substituted phenyl ring system with Z being hydrogen or halogen (as for $R^1$), or $R^1$ can be taken together with $R^3$ to form a fused cyclohexenyl ring or an $X^1$–$X^4$ tetrasubstituted phenyl ring with $X^1$–$X^4$ being independently selected from hydrogen, halogen or nitro; $R^2$ is $C_{1-4}$ alkyl, Z-substituted phenyl with Z as defined above, or absent when $R^1$ and $R^3$ form a fused pheny ring system, or taken together with $R^1$ to form an alkylene bridge as defined above; $R^3$ is $H_2$ or can be taken together with $R^1$ to form a fused phenyl ring as defined above; B is an $R^4$, $R^5$-disubstituted heterocyclic ring system chosen from the group consisting of benzisothiazole, pyridine, and pyrimidine, with $R^4$ and $R^5$ being independently selected from $C_{1-4}$ alkyl, $C_{1-4}$ alkoxy, $C_{1-4}$ alkylthio, cyano, halogen, or hydrogen; and n is 2–4.

Selected compounds exemplary of the hereinabove-described structural variations have displayed useful psychotropic properties which include reversal of drug-induced catalepsy, and tranquilizing activity characterized by antianxiety and/or antipsychotic action.

DETAILED DESCRIPTION OF THE INVENTION

The compounds comprising this invention correspond in structure to I, shown and described hereinabove. Contemplated classes of compounds are distinguished by the substituted 2,5-pyrrolidinedion-1-yl moiety, the instant compounds belonging to one of three structural subclassifications (1, 2, or 3).

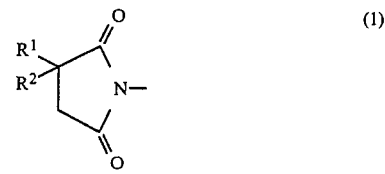

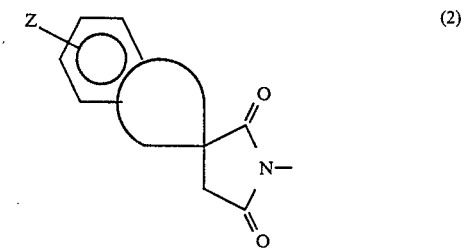

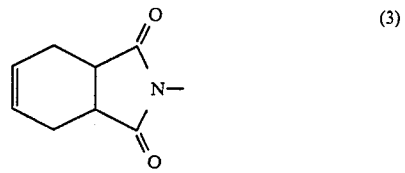

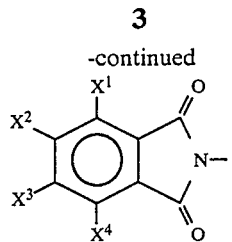

In these structures, $R^1$ and $R^2$ are independently selected from $C_{1-6}$ alkyl, trifluoromethyl, and Z-substituted phenyl; $X^1$-$X^4$, and Z are as defined hereinabove. More detailed depictions of structures representing (2), a preferred class, are shown below wherein B (of Formula I) is 2-pyrimidinyl.

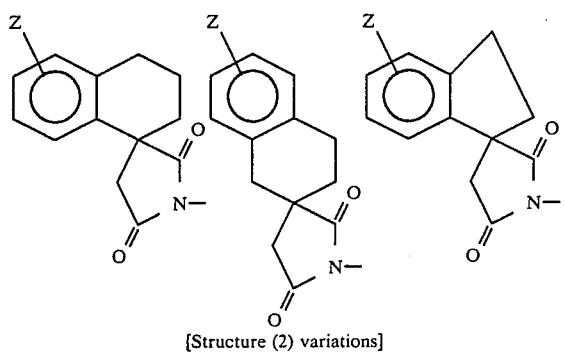

[Structure (2) variations]

It is to be understood that, as used herein, halogen denotes fluorine, iodine, and preferably chlorine and bromine with the symbol "$C_{1-4}$" referring to both straight and branched chain carbon radicals of from 1 to 4 carbon atoms inclusive.

Pharmaceutically acceptable acid addition salts of the invention are those in which the anion does not contribute significantly to the toxicity or pharmacological activity of the salt and, as such they are the pharmacological equivalents of the bases of Formula I. These are generally preferred for medical usage. In some instances, these have physical properties which make them more desirable for pharmaceutical formulation such as solubility, lack of hygroscopicity, compressibility with respect to tablet formation and compatibility with other ingredients with which the substances may be used for pharmaceutical purposes. The salts are routinely made by mixture of the Formula I base with the selected acid preferably by contact in solution employing an excess of commonly used inert solvents such as water, ether, benzene, alcohol, e.g. ethanol, ethyl acetate, acetonitrile, and so forth. The salts may also be made by methathesis or treatment with an ion exchange resin under conditions in which the anion of one salt of the substance of the Formula I is replaced by another anion under conditions which allow for separation of the desired species such as by precipitation from solution or extraction into a solvent, or elution or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, mandelic, nitric, mucic, isethionic, palmitic, heptanoic, and others.

A unitary process comprehending several method embodiments (A, B, and C) may be employed for preparation of compounds of Formula I. These methods may be adapted to variation in order to produce other compounds embraced by this invention but not specifically disclosed. Variations of the methods to produce the same compounds in somewhat different fashion will also be evident to one skilled in the art. Certain examples will be given for specific illustration.

UNITARY PROCESS

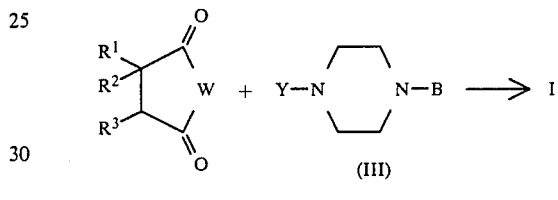

In this scheme, $R^1$, $R^2$, $R^3$, and B have the same meanings as previously assigned to them in Formula I. The symbol "W" can be $>O$; $>NH$; or $>N$—$(CH_2)_n$—Q; with n being 2-4. The symbol "Y" can be $H_2N$—$(CH_2)_n$—; Q—$(CH_2)_n$—;

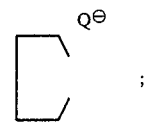

or H; The relationship between W and Y is:

| Method No. | A | B | C |
|---|---|---|---|
| when W is: | $>O$ (IIa) | $>NH$ (IIb) | $>N$—$(CH_2)_n$—Q (IIc) |
| then Y is: | $H_2N$—$(CH_2)_n$— (IIIa) | Q—$(CH_2)_n$— (IIIb) | $Q^\ominus$ (IIIb') or H (IIIc) |

The symbol "Q" refers to a suitable displacement group such as chloride, bromide, iodide, sulfate, phosphate, tosylate, mesylate, or the like.

Method A

-continued

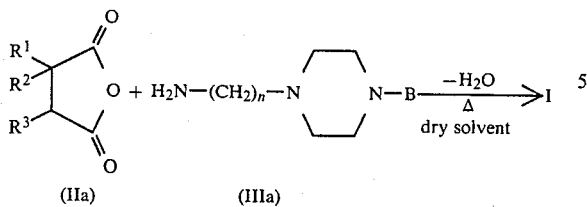

(IIa)    (IIIa)

Method B

1. 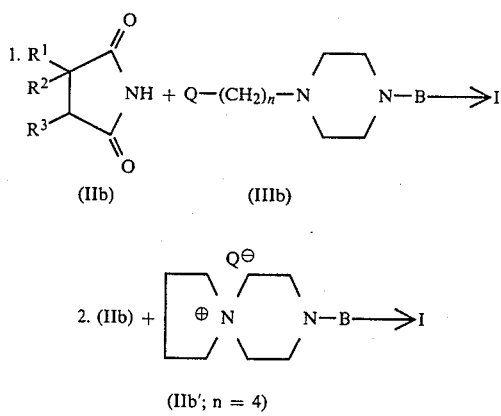

(IIb)    (IIIb)

(IIb'; n = 4)

Method C

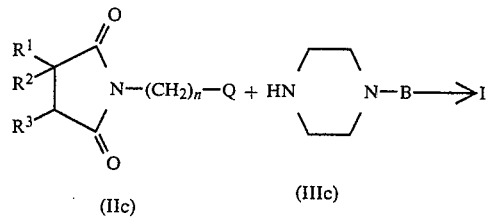

(IIc)    (IIIc)

The condensation process in method A is carried out by refluxing the reactants in a dry, inert reaction medium such as pyridine or xylene. For methods B and C the process is carried out under reaction conditions suitable for the preparation of tertiary amines by alkylation of secondary amines. The reactants are heated in a suitable organic liquid at temperatures of about 60° C. to about 150° C. in the presence of an acid binding agent. Benzene, dimethylformamide, ethanol, acetonitrile, toluene, and n-butyl alcohol are preferred examples of the organic liquid reaction media. The preferred acid binding agent is potassium carbonate, but other inorganic and tertiary organic bases may be employed including other alkali and alkaline earth metal carbonates, bicarbonates, or hydrides, and the tertiary amines. All three methods have been adequately described by Wu, et al. in the cited patents and articles listed above and these are hereby incorporated in entirety by reference. As an example of a method variation (Method D) to produce the same compounds somewhat differently, an N-substituted piperazinylalkylpyrrolidinedione (VI) can be reacted with an appropriate B system (VII) to yield a product of Formula I, e.g.

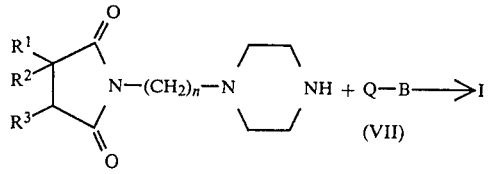

(VI)

The intermediate succinic acid anhydrides or succinimides (2,5-pyrrolidinediones) of Formula II (1) or (2), are either commercially available, found in the chemical literature or described briefly herein. The general synthesis of these intermediate compounds is illustrated in the following scheme.

PREPARATION OF (II) INTERMEDIATES

Scheme 1
General Synthesis

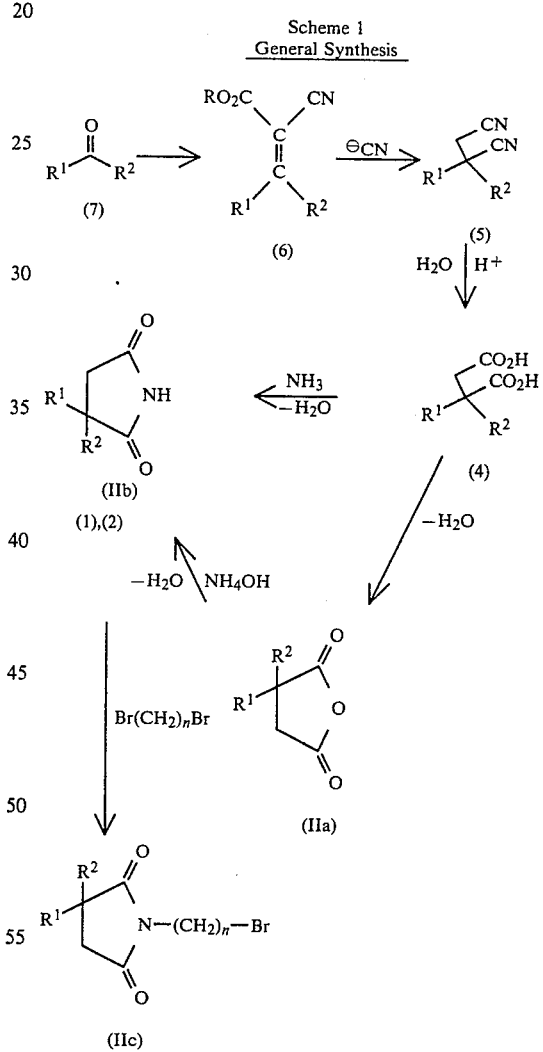

In Scheme 1 shown above, $R^1$ and $R^2$ are as previously defined. Essentially, Scheme 1 is comprised of a Knoevenagel-condensation of a ketone or aldehyde with ethylcyanoacetate to yield a variety of $\alpha,\beta$-unsaturated cyanoacetates (6). Reaction of (6) with about 1½ to 2 equivalents of potassium cyanide affords the dicyano intermediate (5) which undergoes acid-catalyzed hydrolysis to give the dicarboxylic acid intermediate (4). The standard method of imide ring closure of a dicarboxylate compound, aminolysis followed by dehydration, was used. In this manner the (1), (2) types of (II) intermediates can be obtained. The above general synthesis, in terms of its individual reactions, is more fully described in the following references:

1. New and Yevich, *Synthesis,* 1983, No. 5, 388–389.
2. Crooks and Sommerville, *J. Pharm. Sci.,* 71, 291 (1982).
3. *Org. Syn. Collective Vol.* 3, 615–616.
4. *Chemical Abstracts,* 82, 170573x (1975).

Phthalimides and tetrahydrophthalimide intermediates (3) are generally commercially available. Methods for their preparation are also available in the chemical literature.

The piperazine intermediates (III) are described in the aforementioned Wu, et al. and Temple, et al. patents and certain references cited therein, as well as the Temple patent applications, cited hereinabove. These procedures are applicable to the preparation of other piperazine intermediates not specifically disclosed therein but which are required as intermediates for the present invention. Necessary modifications of the above methods to prepare other piperazine intermediates would be well within the skill of a chemical practitioner.

The compounds of the instant invention are pharmacological agents with psychotropic properties. In this regard, they exhibit tranquilizing activity at non-toxic doses and are of particular interest as anxiolytic and/or antipsychotic agents. Compounds of the instant invention also are active in reversing catalepsy. Selected in vivo and in vitro animal tests confirm that preferred Formula I compounds, wherein B is a 2-pyrimidinyl moiety, possess anxiolytic activity and/or antipsychotic action. The following in vivo screening tests were utilized as the basis to determine the tranquilizing profile and potential side-effect liabilities of the instant compounds.

| Behavioral Test | Reference |
| --- | --- |
| Suppression of Conditioned Avoidance Response (CAR) | Albert, Pharmacologist, 4, 152 (1962); Wu, et al., J. Med. Chem., 12, 876–881 (1969). |
| Catalepsy | Costall, et al., Psychopharmacologia, 34, 233–241 (1974); Birkson, J. Amer. Statist. Assoc., 48, 565–599 (1953). |
| Protection Against Norepinephrine Lethality | Loew, et al., J. Pharmacol. Exp. Ther., 93, 434–445 (1948) |

As further indication of the psychotropic activity and specificity of the instant compounds, state of the art in vitro central nervous system receptor binding methodology can be employed. Certain compounds (commonly referred to ligands) have been identified which preferentially deal to specific high affinity sites in brain tissue associated with psychotropic activity or potential for side effects. Inhibition of radiolabeled ligand binding to such specific high affinity sites is considered a measure of a compound's ability to affect corresponding central nervous system functions or cause side effects in vivo. This principle is employed in the following in vitro assay which is given by way of example.

| Receptor Binding Assay | Reference |
| --- | --- |
| Dopamine | Burt, et al., Molec. Pharmacol., 12, 800 (1976); Science, 196, 326 (1977); Creese, et al., Science, 192, 481 (1976). |

According to the pharmacological profile established by the aforementioned tests, representative compounds of Formula I have promising tranquilizing potential, either antianxiety and/or antipsychotic activity, in that they are relatively potent in the CAR test, having oral $ED_{50}$ values $<100$ mg/kg body weight. Many of these are also largely inactive in dopamine binding, having $IC_{50}$'s of $>1000$ nanomolar in the $^3H$ spiperone dopamine receptor binding assay. Activity in the CAR test with only weak activity in this spiperone assay is considered predictive of selective anxiolytic potential in man. Concerning prediction of side-effect liability, certain Formula I compounds wherein $R_3$ is $H_2$ show activity in the reversal of trifluoperazine-induced catalepsy test by virtue of $ED_{50}$ values being $<20$ mg/kg, p.o. Activity in this test suggests that the compounds lack the potential for eliciting the unwanted side effects associated with extrapyramidal symptomatology. Another test predictive of side effects measures protection against norepinephrine lethality. This procedure essentially relates to alpha-block and the unwanted side effects which accompany it, such as sedation and blood pressure lowering. For the instant series of compounds, very little activity in this test is detected with $ED_{50}$ values being $>100$ mg/kg for most members of this series.

As examples of compounds whose pharmacological profile indicate selective anxiolytic potential, two preferred members are 1'-[4-[4-(2-pyrimidinyl)-1-piperazinyl]butyl]spiro[1,2,3,4-tetrahydronaphthylene-2,3'-pyrrolidine-2',5',-dione] (Example 16) and 3,3-diphenyl-1-[4-[4-(2-pyrimidinyl)-1-piperazinyl]butyl]-2,5-pyrrolidinedione (Example 9). Two preferred compounds with expectations for potential non-dopaminergic antipsychotic activity are 3-(4-fluorophenyl)-3-methyl-1-[4-[4-(2-pyrimidinyl)-1-piperazinyl]butyl]-2,5-pyrrolidinedione (Example 7) and 1'-[4-[4-(2-pyrimidinyl)-1-piperazinyl]butyl]spiro[2,3-dihydro-1H-indene-1,3'-pyrrolidine-2',5'-dione] (Example 31).

Another aspect of the instant invention provides a method for treating a mammal afflicted with anxiety or psychosis which comprises administering systemically to said mammal a therapeutically effective tranquilizing amount of a compound of Formula I or a pharmaceutically acceptable acid addition salt thereof. An effective dose ranges from approximately 0.01 to 40 mg/kg of body weight with a dosage dependent on effects sought, manner of administration, and to some extent with a particular compound selected. A preferred dosage range is considered to be about 0.5 to 1.5 mg/kg per day, given in divided doses. Systemic administration refers to oral, rectal and parenteral (i.e. intramuscular, intravenous and subcutaneous). Generally, it will be found that when a compound of the present invention is administered orally, a larger quantity of the active agent is required to produce the same effect as a smaller quantity given parenterally. In accordance with good clinical practice, it is preferred to administered the instant compounds at a concentration level that will produce effective anxiolytic effects without causing any harmful or untoward side effects.

The compounds of the present invention may be administered for anxiolytic purposes either as individual therapeutic agents or as mixtures with other therapeutic agents. Therapeutically, they are generally given as pharmaceutical compositions comprised of an antidepressant amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. syrups, acacia, gelatin, sorbitol, tragacanth, or polyvinylpyrrolidone); fillers, (e.g. lactose, sugar, maize-starch, calcium phosphate, sorbitol or glycine); lubricants (e.g. magnesium stearate, talc, polyethylene glycol or silica); disintegrants (e.g. starch); and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonances (NMR) spectral characteristics refer to chemical shifts ($\delta$) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported as broad singlet (bs), singlet (s), multiplet (m) or doublet (d). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

EXAMPLE 1

Ethyl 2-Cyano-3-methyl-3-phenyl-2-propenoate (6)

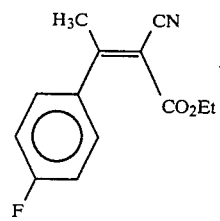

A mixture of p-fluoroacetophenone (100 g, 0.72 mole), ethyl cyanoacetate (81.8 g, 0.72 mole), ammonium acetate (13 g, 0.17 mole) and acetic acid (34.7 g, 0.57 mole) is refluxed for 24 hours in benzene (200 mL) with a continuous removal of water by a Dean Stark trap. The cooled mixture is diluted with benzene (150 mL) and extracted with water (2×300 mL). The organic phase is separated, dried (Na$_2$SO$_4$), filtered and concentrated in vacuo to a brown oil. Kugelrohr distillation (125°–127°/0.03 Torr.) affords 108.4 g (64.3%) of product as a yellow green oil.

EXAMPLE 2

2-(4-Fluorophenyl)-2-methyl-butanedinitrile (5)

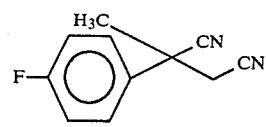

A solution of the product of Example 1 above (50 g, 0.21 mole) and potassium cyanide (24.7 g, 0.38 mole) is refluxed 5 hours in 90% aqueous ethanol (500 mL). The cooled solution is concentrated in vacuo to a gummy solid which is dissolved in chloroform (250 mL) and extracted with water (2×250 mL). The organic phase is separated, dried (Na$_2$SO$_4$), filtered and concentrated in vacuo to a brown oil. Kugelrohr distillation of this material affords 21.7 g (57.6%) of product as a light yellow oil.

EXAMPLE 3

2-(4-Fluorophenyl)-2-methylbutanedioic Acid (4)

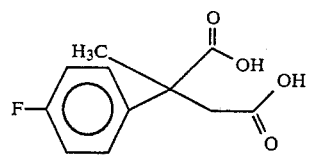

A solution of the dinitrile product of Example 2 (9.0 g, 0.05 mole) and sodium hydroxide (20.0 g, 0.50 mole) is refluxed 36 hours in 40% aqueous ethanol (200 mL). The cooled solution is made strongly acidic with conc. HCl and extracted with ethyl ether (3×250 mL). The organic extracts are combined, dried (Na$_2$SO$_4$), and concentrated in vacuo to a white solid. The solid was recrystallized from water (50 mL) affording 6.1 g (98%) of product as a white solid, m.p. 149°–152.5°.

EXAMPLE 4

2-(4-Fluorophenyl)-2-methylsuccinic Acid Anhydride

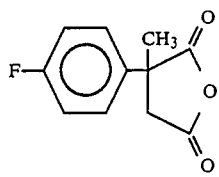 (IIa)

A solution of the diacid prepared in Example 3 (7 g, 0.034 mole) in 18 g of acetic anhydride was refluxed for 3 hours producing a light brown solution. The reaction mixture was concentrated in vacuo to the product as a syrup. This syrupy anhydride may be used without further purification or purified by distillation.

EXAMPLE 5

2-(4-Fluorophenyl)-2-methylsuccinimide

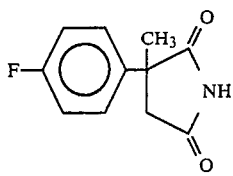 (IIb)

The succinic acid anhydride product prepared in Example 4 (6 g, 0.029 mole) was mixed with 25 g of NH4OH leading to a vigorous exothermic reaction. After the spontaneous reaction had subsided the mixture of ammonium hydroxide containing white solid was warmed to 120° for 30 minutes. The excess ammonium NH4OH was removed in vacuo and the residual material was heated at 200° for approximately 45 minutes at which time steam evolution ceased. Upon cooling, the clear melt solidified to a white substance which was recrystallized from isopropyl alcohol. A total of 5.5 g (91%) of succinimide product was obtained.

EXAMPLE 6

3-(4-Fluorophenyl)-3-methyl-1-[4-[1-piperazinyl]butyl]-2,5-pyrrolidinedione

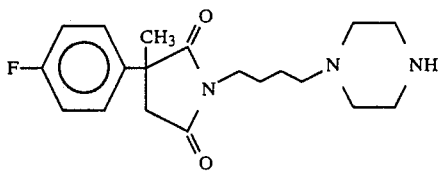 (VI)

A mixture of the succinimide prepared in Example 5 (14.2 g, 0.06 mole), 1,4-dibromobutane (37.0 g, 0.17 mole) and potassium carbonate (15.8 g, 0.11 mole) is stirred for 12 hours and refluxed in acetonitrile (200 mL). The solution is filtered and concentrated in vacuo to 1-(4-bromobutyl)-3-(4-fluorophenyl)-3-methyl-2,5-pyrrolidinedione (IIc) as an oil. The oil may be used as is or purified further by Kugelrohr distillation.

A mixture of the IIc product (28.2 g, 0.08 mole), piperazine (35.4 g, 0.41 mole) and potassium carbonate (34.1 g, 0.25 mole) is refluxed 48 hours in acetonitrile (250 ml). The reaction mixture is filtered and concentrated in vacuo to an oil which is partitioned between chloroform and water. The organic phase is separated, dried (Na2SO4), filtered and concentrated in vacuo to an oil which is dissolved in ethanol (100 mL) and treated with ethanolic hydrochloric acid (7N). Upon cooling, 27.0 g (80.5%) of product as a white dihydrochloride salt is collected, m.p. 240°–247°.

EXAMPLE 7

3-(4-Fluorophenyl)-3-methyl-1-[4-[4-(2-pyrimidinyl)-1-piperazinyl]butyl]-2,5-pyrrolidinedione

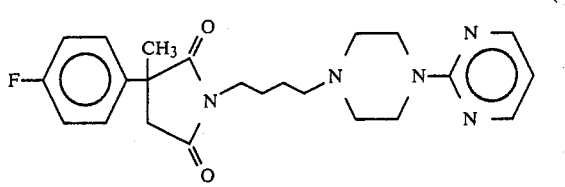 I-(1)

A mixture of the piperazine product (VI) prepared above in Example 6 (6.0 g, 0.014 mole), 2-chloropyrimidine (1.67 g, 0.014 mole) and potassium carbonate (3.8 g, 0.028 mole) is refluxed 12 hours in acetonitrile (100 mL). The solution is filtered, reduced slightly in volume, and treated with ethanolic hydrochloric acid (7N). Cooling leads to crystallization of the hydrochloride salt which is collected as a white solid (4.5 g, 74.2%), m.p. 160°–163° (dec).

Anal. Calcd. for $C_{25}H_{28}FN_5O_2 \cdot HCl$: C, 61.79; H, 6.02; N, 14.42. Found: C, 61.68; H, 5.96; N, 14.11.

NMR (DMSO-$d_6$): 1.64 (3,s); 1.67 (4,m); 3.01 (2,s); 3.12 (4,m); 3.49 (6,m); 4.25 (2,m); 7.25 (5,m); 8.14 (1,dd, [2.0, 7.8 Hz]); 8.46 (1,dd [2.0, 5.0 Hz]); 11.68 (1,bs).

IR (KBr): 835, 1230, 1440, 1510, 1555, 1590, 1695, 1775, 2210, 2560, and 2940 cm$^{-1}$.

This above synthetic method represents the procedure for preparing I compounds by Method D as discussed supra. The same product can be prepared by suitable adaptation of the other methods A–C. To illustrate Method B:

A mixture of the succinimide prepared in Example 5 (2.2 g, 0.01 mole), 8-(2-pyrimidinyl)-8-aza-5-azoniaspiro[4.5]decane bromide (IIIb′, 3.0 g, 0.01 mole) and potassium carbonate (3.3 g, 0.024 mole) were refluxed 36 hours in dimethylformamide. The cooled solution was filtered, concentrated in vacuo to a syrup which was dissolved in chloroform and extracted (2×100 mL) with water. The organic phase was dried (Na2SO4), filtered, and concentrated in vacuo to a yellow syrup which was purified by chromatography, eluting with 20% ethanolchloroform. Isolation of material from the desired chromatographic fractions were dissolved in isopropanol and converted with ethanolic HCl into the desired product as characterized above.

EXAMPLE 8

2-[4-[4-[5-Fluoro-4-(methylthio)-2-pyrimidinyl]-1-piperazinyl]butyl]-1H-isoindole-1,3(2H)-dione

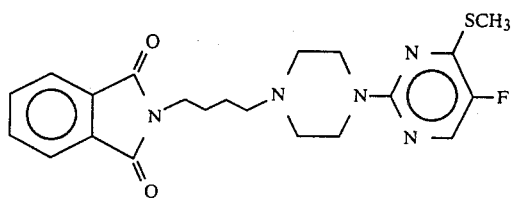

I-(3)

A mixture of 8-(5-fluoro-4-methylthio-2-pyrimidinyl)-8-aza-5-azoniaspiro[4.5]decane bromide (9.76 g, 0.027 mole) and phthalimide potassium salt (5.0 g, 0.027 mole) is refluxed 16 hours in dimethylformamide (100 mL). Th volatiles are removed in vacuo and the mixture is dissolved in chloroform (100 mL) and extracted with water (2×50 mL). The organic phase is separated, dried ($Na_2SO_4$), filtered and concentrated in vacuo to a gum which is dissolved in ethanol (50 mL) and treated with ethanolic HCl. Product crystallizes upon cooling to yield 12.9 g (93.0%) of product as a white solid hydrochloride salt, m.p. 235°–237°.

Anal. Calcd. for $C_{21}H_{24}FN_5O_2S \cdot HCl$: C, 54.14; H, 5.41; N, 15.03. Found: C, 54.25; H, 5.34; N, 15.06.

NMR (DMSO-$d_6$): 1.73 (4,m); 2.51 (3,s); 3.09 (4,m); 3.58 (6,m); 4.59 (2,m); 7.86 (4,m); 8.19 (1,d [1.8 Hz]); 11.63 (1,bs).

IR (KBr): 725, 1440, 1500, 1550, 1585, 1715, 1770, 2500, and 2940 cm$^{-1}$.

EXAMPLE 9

3,3-Diphenyl-1-[4-[4-(2-pyrimidinyl)-1-piperazinyl]-butyl]-2,5-pyrrolidinedione

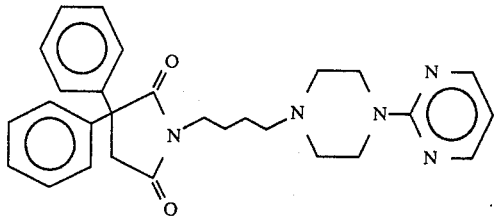

I-(1)

A mixture of 1-(4-bromobutyl)-3,3-diphenyl-2,5-pyrrolidinedione [(prepared by reaction of 3,3-diphenyl-2,5-pyrrolidinedione with 1,4-dibromobutane and potassium carbonate in refluxing acetonitrile) 4.1 g, 0.01 mole], 1-(2-pyrimidinyl)piperazine (1.75 g, 0.01 mole) and potassium carbonate (2.94 g, 0.02 mole) is refluxed in acetonitrile (300 mL) for 12 hours. The solution is filtered and concentrated in vacuo to an oil which is partitioned between water and chloroform. The organic phase is separated, dried ($Na_2SO_4$), filtered, and concentrated to an oil which is dissolved in isopropanol. Treatment of this solution with ethanolic HCl leads to crystallization of the white hydrochloride salt (4.2 g, 83%), m.p. 201.5°–203.5°.

Anal. Calcd. for $C_{28}H_{31}N_5O_2 \cdot HCl$: C, 66.46; H, 6.38; N, 13.84. Found: C, 66.31; H, 6.42; N, 13.64.

NMR (DMSO-$d_6$): 1.64 (4,m); 3.05 (4,m); 3.50 (6,m); 3.60 (2,s); 3.68 (2,m); 6.74 (1,t [4.4 Hz]); 7.34 (10,s); 8.45 (2,d [4.4 Hz]); 11.78 (1,bs).

IR (KBr): 700, 765, 1445, 1495, 1550, 1585, 1700, 1775, 2450, and 2940 cm$^{-1}$.

EXAMPLE 10

Ethyl 1,2,3,4-Tetrahydro naphthalene-2,2'-cyanoacetate (6)

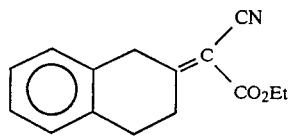

A mixture of 125 g (0.85 mole) of β-tetralone, 96.15 g (0.85 mole) of ethyl cyanoacetate, 15.2 g (0.197 mole) of ammonium acetate, and 42 g (0.70 mole) of acetic acid was refluxed 24 hours in benzene (200 mL) with a continuous removal of water by Dean Stark trap. The cooled reaction mixture was eluted with additional benzene (200 mL) and extracted (3×250 mL) with water. The organic layer was dried ($Na_2SO_4$), concentrated in vacuo, and distilled to give an orange syrup (80 g, 39% yield), b.p. 172°–185°; 0.1 Torr. The syrup solidified upon cooling and was recrystallized from benzene to give a cream colored solid, m.p. 94°–103°.

EXAMPLE 11

1,2,3,4-Tetrahydronaphthalene-2,2'-butanedinitrile (5)

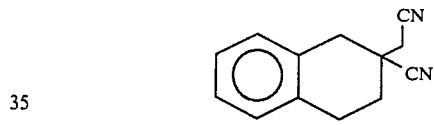

A mixture of the intermediate prepared above in Example 10 (79.8 g, 0.33 mole); potassium cyanide (41.7 g, 0.64 mole) in 65% aqueous ethanol (500 mL) was refluxed 48 hours. The dark solution was concentrated in vacuo to a dark syrup which was dissolved in chloroform (400 mL) and extracted (3×100 mL) with water. The organic phase was dried ($Na_2SO_4$), filtered, and concentrated in vacuo to a dark syrup. The syrup was distilled to give product as a green yellow syrup (38.7 g, 60% yield), b.p. 145°–153° at 0.2 Torr. Upon standing the surface solidified to give solid, m.p. 75°–79°.

EXAMPLE 12

1,2,3,4-Tetrahydronaphthalene-2,2'-butanedioic Acid (4)

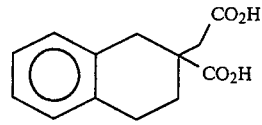

A solution of sodium hydroxide (108 g, 2.7 mole) and 36.0 g (0.18 mole) of the dinitrile product prepared in Example 11, was heated at reflux for 48 hours in 30% aqueous ethanol (700 mL). The solution was then slowly acidified with conc. HCl and, upon cooling, was extracted with chloroform (3×250 mL). The organic washings were combined, dried ($Na_2SO_4$), filtered, and concentrated in vacuo yielding 41 g (97.6% yield) of the product dried as an off white solid.

EXAMPLE 13

Spiro-1,2,3,4-tetrahydronaphthalene-2,3-succinic Acid Anhydride

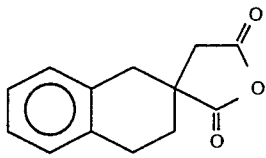 (IIa)

A mixture of the diacid intermediate (prepared above in Example 12, 35 g, 0.149 mole) and a three-fold excess (by weight) of acetic anhydride was refluxed 12 hours resulting in a dark brown solution. The solution was cooled and the excess acetic anhydride distilled in vacuo. The resulting dark mass solidified to give 32 g (99% yield) of crude product. Recrystallization from chloroform-Skelly B gave a white solid (m.p. 98°–100.5°).

EXAMPLE 14

Spiro-1,2,3,4-tetrahydronaphthalene-2,3'-pyrrolidine-2',5'-dione

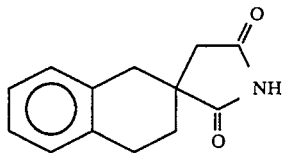 (IIb)

A solution of the succinic anhydride intermediate (prepared above in Example 13, 32.0 g, 0.148 mole) in acetonitrile (250 mL) and a five-fold excess (by weight) of 30% ammonium hydroxide was refluxed 2.5 hours and then concentrated in vacuo to a dark gum. The gum was mixed with xylene and refluxed under a Dean-Stark trap until the evolution of water had ceased (approximately 4 hours). The dark solution was concentrated in vacuo to a solid which was recrystallized from isopropanol (130 mL) affording 24 g (75.4%) of product as an off-white solid, m.p. 234°–236°.

EXAMPLE 15

1'-(4-Bromobutyl)spiro(1,2,3,4-tetrahydro naphthalene-2,3'-pyrrolidine-2',5'-dione)

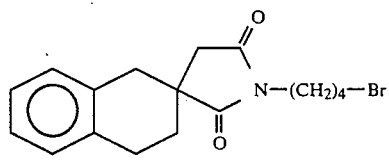

A solution of the succinimide intermediate (prepared above in Example 14, 22.5 g, 0.104 mole); 1,4-dibromobutane (29.1 g, 0.135 mole); and potassium carbonate (41.4 g, 0.3 mole) was refluxed 20 hours in acetonitrile (300 mL). The solution was filtered and concentrated in vacuo to an amber syrup. Distillation of the syrup afforded 18 g (49.5%) of a light viscous syrup, b.p. 185°–220° at 0.1 Torr.

EXAMPLE 16

1'-[4-[4-(2-Pyrimidinyl)-1-piperazinyl]butyl]-spiro[1,2,3,4-tetrahydronaphthalene-2,3'-pyrrolidine-2',5'-dione]

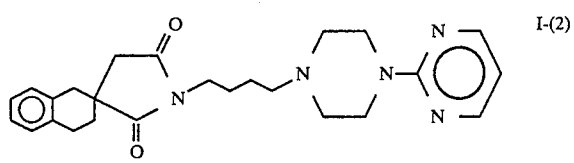 I-(2)

A mixture of the butylbromide intermediate (prepared above in Example 15, 3.9 g, 0.011 mole) and 1-(2-pyrimidinyl)piperazine (1.82 g, 0.011 mole) was heated in acetonitrile (100 mL) for 24 hours with 2.76 g (0.02 mole) of potassium carbonate. The hot solution was filtered and concentrated in vacuo to a solid which was dissolved in chloroform (100 mL) and extracted with water (2×100 mL). The organic phase was separated, dried ($Na_2SO_4$), filtered, and concentrated in vacuo to a solid which was dissolved in acetonitrile (40 mL) and treated with 1.62 mL of 7N ethanolic HCl. Cooling lead to crystallization of 3.5 g (68.6% yield) of a white solid which was recrystallized from acetonitrile-ethanol (2:1) to give the product as a hydrochloride salt, m.p. 241°–243.5°.

Anal. Calcd. for $C_{25}H_{31}N_5O_2 \cdot HCl$: C, 63.89; H, 6.86; N, 14.90. Found: C, 63.76; H, 6.79; N, 14.68.

NMR (DMSO-$d_6$): 1.76 (6,m); 2.36 (1,d [17.6 Hz]); 2.72 (1,d [17.6 Hz]); 3.00 (8,m); 3.44 (6,m); 4.67 (2,m); 6.72 (1,t [4.5 Hz]); 7.09 (4,m); 8.42 (2,d [4.5 Hz]); 11.75 (1,bs).

IR (KBr): 750, 1440, 1550, 1585, 1700, 1770, 2500, and 2930 cm$^{-1}$.

The following products of Formula I can be prepared according to the synthetic schemes and specifically exemplified hereinabove.

Additional Products

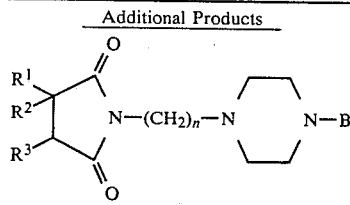

I

| Ex. No. | R¹ | R² | R³ | n | B | m.p.(°C.) |
|---|---|---|---|---|---|---|
| | | | Subclass 1 | | | |
| 17 | phenyl | methyl | H₂ | 4 | 2-pyrimidinyl | 190–200 |
| 18 | p-fluorophenyl | methyl | H₂ | 2 | 2-pyrimidinyl | 214–216 |
| 19 | p-fluorophenyl | methyl | H₂ | 3 | 2-pyrimidinyl | 185–189 |
| 20 | p-fluorophenyl | methyl | H₂ | 4 | 2-(3-cyanopyridyl) | 168–170.5 |
| 21 | p-fluorophenyl | methyl | H₂ | 4 | 3-benzisothiazolyl | 188–189.5 |
| 22 | phenyl | trifluoromethyl | H₂ | 4 | 2-pyrimidinyl | 185–186 |
| 23 | phenyl | phenyl | H₂ | 4 | 2-(3-cyanopyridyl) | 179–182 |
| 24 | phenyl | phenyl | H₂ | 4 | 3-benzisothiazolyl | 188–189.5 |
| 25 | phenyl | ethyl | H₂ | 3 | 5-fluoro-2-pyrimidinyl | |
| | | | Subclass 2 | | | |
| 26 | 1-(1,2,3,4-tetrahydronaphthalene) | | H₂ | 4 | 2-pyrimidinyl | 241–247 |
| 27 | 1-(1,2,3,4-tetrahydronaphthalene) | | H₂ | 4 | 2-(3-cyanopyridyl) | 196–198 |
| 28 | 1-(1,2,3,4-tetrahydronaphthalene) | | H₂ | 4 | 3-benzisothiazolyl | 207–212 |
| 29 | 1-indanyl | | H₂ | 4 | 2-pyrimidinyl | 241–248 |
| 30 | 1-indanyl | | H₂ | 4 | 5-fluoro-2-pyrimidinyl | |
| | | | Subclass 3 | | | |
| 31 | ├─benzo─┤ | | | 4 | 2-pyrimidinyl | 137–139.5 |
| 32 | ├─2,3-dichlorobenzo─┤ | | | 4 | 2-pyrimidinyl | 145–146.5 |
| 33 | ├─1,2,3,4-tetrachlorobenzo─┤ | | | 4 | 2-pyrimidinyl | 154–156 |
| 34 | ├─2-nitrobenzo─┤ | | | 4 | 2-pyrimidinyl | 130–133 |
| 35 | ├─1,4,5,6-tetrahydrobenzo─┤ | | | 4 | 2-pyrimidinyl | 209–210 |
| 36 | ├─2-nitrobenzo─┤ | | | 4 | 2-(3-cyanopyridyl) | 205–208 |
| 37 | ├─benzo─┤ | | | 2 | 5-fluoro-2-pyrimidinyl | |
| 38 | ├─benzo─┤ | | | 3 | 5-chloro-2-pyrimidinyl | |

What is claimed is:

1. A compound having Formula I

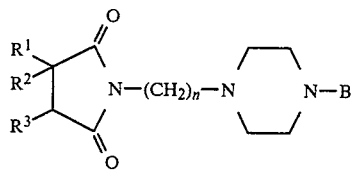

wherein

R¹ is $C_{1-4}$ alkyl, trifluoromethyl, Z-substituted phenyl with Z being hydrogen or halogen or R¹ can be taken together with R² as a $C_{4-5}$ alkylene bridge incorporating a fused Z-substituted phenyl ring system, Z being hydrogen or halogen or R¹ can be taken together with R³ to form a fused cyclohexenyl ring or an $X^1$–$X^4$ tetra-substituted phenyl ring with $X^1$–$X^4$ being independently selected from hydrogen, halogen or nitro;

R² is $C_{1-4}$ alkyl, Z-substituted phenyl with Z as defined above, or absent when R¹ and R³ form a fused phenyl ring system, or taken together with R¹ to form an alkylene bridge as defined above;

R³ is H₂ or can be taken together with R¹ to form a fused phenyl ring as defined above;

B is an $R^4$,$R^5$-disubstituted heterocyclic ring system chosen from the group consisting of benzoisothiazole, pyridine, and pyrimidine, with $R^4$ and $R^5$ being independently selected from $C_{1-4}$ alkyl, $C_{1-4}$ alkoxy, $C_{1-4}$ alkylthio, cyano, halogen, or hydrogen; and n is 2–4;

or a pharmaceutically acceptable acid addition salt thereof.

2. The compound of claim 1 wherein R¹ is $C_{1-4}$ alkyl, trifluoromethyl, Z-substituted phenyl with Z being hydrogen or halogen; R² is Z-substituted phenyl; and R³ is H₂.

3. The compound of claim 1 wherein $R^1$ and $R^2$ are taken together as a $C_{4-5}$ alkylene bridge incorporating a fused Z-substituted phenyl ring system with Z being hydrogen or halogen; and $R^3$ being $H_2$.

4. The compound of claim 1 wherein $R^1$ and $R^3$ form a fused cyclohexenyl ring or an $X^1$–$X^4$ tetra-substituted phenyl ring with $X^1$–$X^4$ being independently selected from hydrogen, halogen, or nitro; and $R^2$ is absent.

5. The compound of claim 1 wherein B is 2-pyrimidinyl.

6. The compound of claim 2 which is 3-methyl-3-phenyl-1-[4-[4-(2-pyrimidinyl)-1-piperazinyl]butyl]-2,5-pyrrolidinedione or a pharmaceutically acceptable acid addition salt thereof.

7. The compound of claim 2 which is 3-(4-fluorophenyl)-3-methyl-1-[4-[4-(2-pyrimdinyl)-1-piperazinyl]butyl]-2,5-pyrrolidinedione or a pharmaceutically acceptable acid addition salt thereof.

8. The compound of claim 2 which is 3,3-diphenyl-1-[4-[4-(2-pyrimidinyl)-1-piperazinyl]butyl]-2,5-pyrrolidinedione or a pharmaceutically acceptable acid addition salt thereof.

9. The compound of claim 2 which is 3,3-diphenyl-1-[4-[4-(1,2-benzisothiazol-3-yl)-1-piperazinyl]butyl]-2,5-pyrrolidinedione or a pharmaceutically acceptable acid addition salt thereof.

10. A compound of claim 3 which is 1'-[4-[4-(2-pyrimidinyl)-1-piperazinyl]butyl]spiro[1,2,3,4-tetrahydronaphthalene-2,3'-pyrrolidine-2',5'-dione] or a pharmaceutically acceptable acid addition salt thereof.

11. A compound of claim 3 which is 1'-[4-[4-(2-pyrimidinyl)-1-piperazinyl]butyl]spiro[2,3-dihydro-1H-indene-1,3'-pyrrolidine-2',5'-dione] or a pharmaceutically acceptable acid addition salt thereof.

12. The compound of claim 4 which is 2-[4-[4-(2-pyrimidinyl)-1-piperazinyl]butyl]-1H-isoindole-1,3(2H)-dione or a pharmaceutically acceptable acid addition salt thereof.

13. The compound of claim 2 which is, 1-[4-[4-(1,2-benzisothiazol-3-yl)-1-piperazinyl]butyl]-3-(4-fluorophenyl)-3-methyl-2,5-pyrrolidinedione.

14. The compound of claim 2 which is 3-(4-fluorophenyl)-3-methyl-1-[2-[4-(2-pyrimidinyl)-1-piperazinyl]ethyl]-2,5-pyrrolidinedione.

15. The compound of claim 2 which is 3-(4-fluorophenyl)-3-methyl-1-[3-[4-(2-pyrimidinyl)-1-piperazinyl]propyl]-2,5-pyrrolidinedione.

16. The compound of claim 2 which is 3-phenyl-1-[4-[4-(2-pyrimidinyl)-1-piperazinyl]butyl]-3-(trifluoromethyl)-2,5-pyrrolidinedione.

17. The compound of claim 3 which is 1'-[4[4-(2-pyrimidinyl-1-piperazinyl]butyl]spiro[1,2,3,4-tetrahydronaphthalene-1,3'-pyrrolidine-2',5'-dione].

18. The compound of claim 3 which is 1'-[4-[4-(1,2-benzisothiazol-3-yl)-1-piperazinyl]butyl]spiro[1,2,3,4-tetrahydronaphthalene-1,3'-pyrrolidine-2',5'-dione].

19. The compound of claim 4 which is 3a,4,7,7a-tetrahydro-2-[4-[4-(2-pyrimidinyl)-1-piperazinyl]butyl]-1H-isoindole-1,3-(2H)-dione.

20. The compound of claim 4 which is 4,5,6,7-tetrachloro-2-[4-[4-(2-pyrimidinyl)-1-piperazinyl]butyl]-1H-isoindole-1,3(2H)-dione.

21. The compound of claim 4 which is 5-nitro-2-[4-[4-(2-pyrimidinyl)-1-piperazinyl]butyl]-1H-isoindole-1,3(2H)-dione.

22. The compound of claim 4 which is 5,6-dichloro-2-[4-[4-(2-pyrimidinyl)-1-piperazinyl]butyl]-1H-isoindole-1,3(2H)-dione.

23. The compound of claim 4 which is 2-[4-[4-[5-fluoro-4-(methylthio)-2-pyrimidinyl]-1-piperazinyl]butyl]-1H-isoindole-1,3(2H)-dione.

* * * * *